United States Patent [19]

Bowman et al.

[11] Patent Number: 4,999,772
[45] Date of Patent: Mar. 12, 1991

[54] SLEEP SCREENING SYSTEM WITH TIME BASED MODULATED DATA

[75] Inventors: Bruce R. Bowman, Eden Prairie; Michael R. Oran, Chaska; Gary J. Syring, Lakeville, all of Minn.

[73] Assignee: Eden Tec Corporation, Eden Prairie, Minn.

[21] Appl. No.: 301,233

[22] Filed: Jan. 24, 1989

[51] Int. Cl.⁵ .................... G06F 15/42; A61B 5/0205
[52] U.S. Cl. ............................... 364/413.05; 728/709; 728/711
[58] Field of Search .................. 364/413.05; 346/45, 346/53; 128/671, 709-711, 716

[56] References Cited

U.S. PATENT DOCUMENTS

4,784,162 11/1988 Ricks et al. ........................ 128/903
4,836,219 6/1989 Hobson et al. ..................... 128/782

Primary Examiner—Allen R. MacDonald
Assistant Examiner—Gail O. Hayes
Attorney, Agent, or Firm—Douglas L. Tschida

[57] ABSTRACT

A portable sleep monitoring system for recording on tape, transcribing and charting a plurality of physiologic data channels recorded relative to a known constant, user-transparent time base. Selected ECG, air flow, impedance and pulse oximetry sensor inputs are recorded under microprocessor control relative to a crystal controlled 40 Hz signal modulated with the physiologic data from one of the sensors. Upon reading the physiologic data from tape and/or charting, the collected data is displayed with the time base, normalized to the known crystal controlled timing signal. In the heart rate mode, QRS occurences are displayed on the heart rate trace line as singular hash marks. The presence of motion at the pulse O2 sensor is indicated by multiplexing high frequency hash markings onto the O2 saturation trace line. Calibration levels relating to four different O2 saturation percent vales are periodically written to tape for reference during tape reading.

13 Claims, 8 Drawing Sheets

SLEEP SCREENING SYSTEM WITH TIME BASED MODULATED DATA

BACKGROUND OF THE INVENTION

The present invention relates to a cardio-respiratory recording system and, in particular, to a portable, multi-channel polygraph system for recording and replaying ECG, respiratory effort, respiratory airflow, and oxygen saturation levels in order to document abnormal sleep respiration patterns, most notably apnea.

Traditionally, polysomnography studies have been conducted using either two-channel pneumocardiograms (i.e. ECG and respiratory impedance data) or multi-channel recordings of sixteen to twenty channels. Although performed more conveniently, two-channel recordings are limited in the amount of information they can provide for meaningful diagnosis. Sixteen to twenty channel studies, in contrast, are limited to sleep laboratories with corresponding higher study costs associated with the capital equipment, personnel and plant. A trade-off must thus normally be made by the clinician or diagnostician between limited data, which can produce misdiagnosis or missed significant respiratory events, and almost unlimited data with its greater attendant costs.

Of the systems of which Applicant is aware, sensor data is collected from two to twenty channels relative to a separate time channel, or through calibration of mechanical components of a system which may vary in speed and could effect timing and rate calculations. Data is typically collected and displayed one channel per track without multi-plexing or overlaying physiologically distinguishable data on a single track during replay. For example, heart rate data is either displayed as a singular trace heart rate line at relatively slow chart rates or as individual QRS waveforms at a fast chart rate. Both are not shown together on a single track. Applicant is also not aware of any system particularly displaying heart rate data with a hash or "tic" mark relative to the trend or trace line to indicate the time occurrence of each QRS complex.

Similarly and relative to O2 saturation and motion artifact, applicant is unaware of any system which distinguishes motion from true O2 desaturations. Additionally existing systems do not provide periodic calibration levels as reference points. Such multiplexed data, not only maximizes the data display, but also provides meaningful information to the clinician to permit on going confirmation of the oximetry sensor calibration which may change over the course of a study session.

A need therefore exists for an economical data collection system of fewer than 12 to 20 channels in a portable construction whereby a subject's sleep patterns may be monitored at home or in a clinical setting and which data may be used in evaluating and pre-screening suspected sleep or other cardio-pulmonary disorders. Advantages are thereby attainable to the clinician and third-party payors. In the case of infants and out-patient care, apnea monitoring programs may also be more economically conducted on a longterm basis.

SUMMARY OF THE INVENTION

It is accordingly a primary object of the present invention to provide a portable, low cost, multi-channel cardio-respiratory recorder for home and clinical use for recording and replaying monitored events.

It is a further object of the invention to provide a multi-channel system for recording ECG, respiratory effort (i.e. impedance, strain gage, etc.), respiratory airflow (i.e. nasal/oral thermistry, expired $CO_2$, pressure etc.) pulse/oximetry and other physiologic data (i.e. sophageal PH), relative to a normalized user-transparent time base.

It is a further object of the invention to modulate a 40Hz, crystal oscillator time base signal on one of the channels whereby mechanical speed variations between recorder, scanner and chart paper devices can be negated.

It is a yet further object of the invention to multiplex physiologically distinguishable data onto single charter tracks.

It is a still further object of the invention to provide a system wherein during a heart rate mode, individual QRS events are notated with a hash mark.

It is a yet further object of the invention to provide a system wherein detected pulse/motion data is multiplexed onto sensed oximetry data and whereby confirmation of oximetry calibration can also be obtained.

Various of the above objects, advantages and distinctions of the invention are particularly achieved in a presently preferred system comprising a portable, multi-channel, magnetic tape recorder including input circuitry selectively compatible with a wide variety of physiologic sensors, including ECG, pulse oximetry, thermistry and impedance respiration sensors. The recorder also includes associated microprocessor control circuitry for preparing a four-track data tape, having a time reference produced from a user-transparent normalized time base signal modulated with one of the sensor's data tracks.

Separate charter and tape player apparatus each include means for de-modulating the time base data from one of the physiologic channels and displaying the physiologic data in a hardcopy format in proper time synchronization. Selectable means coupled to the pulse oximetry data permit the multiplexing of the pulse plethysmographic waveform data onto the O2 saturation data prior to charting. Associated QRS detect circuitry, during a heart rate trend mode, and under microprocessor control, causes a hash mark to be printed onto the ECG trend line timed with the occurrence of each QRS complex. The microprocessor also compares collected ECG and pulse plethysmographic data to display motion when they are not equivalent.

Still other objects, advantages and distinctions of the invention, along with its detailed construction, will become more apparent hereinafter upon reference to the following description thereof with respect to the appended drawings. Before referring thereto, it is to be appreciated the following description is made by way of a presently preferred embodiment only, which should not be interpreted in limitation of the spirit and scope of the invention claimed hereinafter. To the extent modifications or improvements have been considered, they are described as appropriate.

DESCRIPTION OF THE PREFERRED EMBODIMENT

Figure 1A:
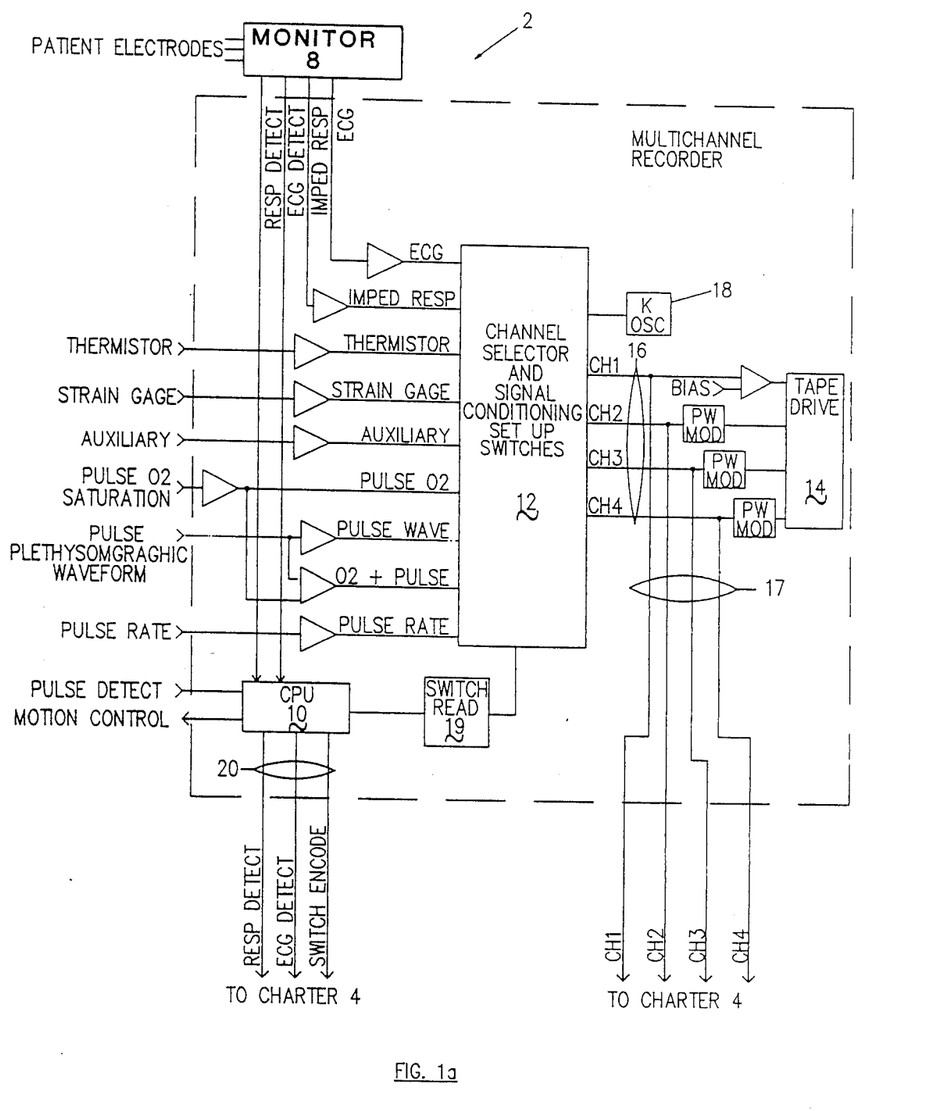
FIGS. 1a, 1b and 1c show functional block diagrams of the respective multi-channel recorder, charter and tape scanner.
Figure 1B:
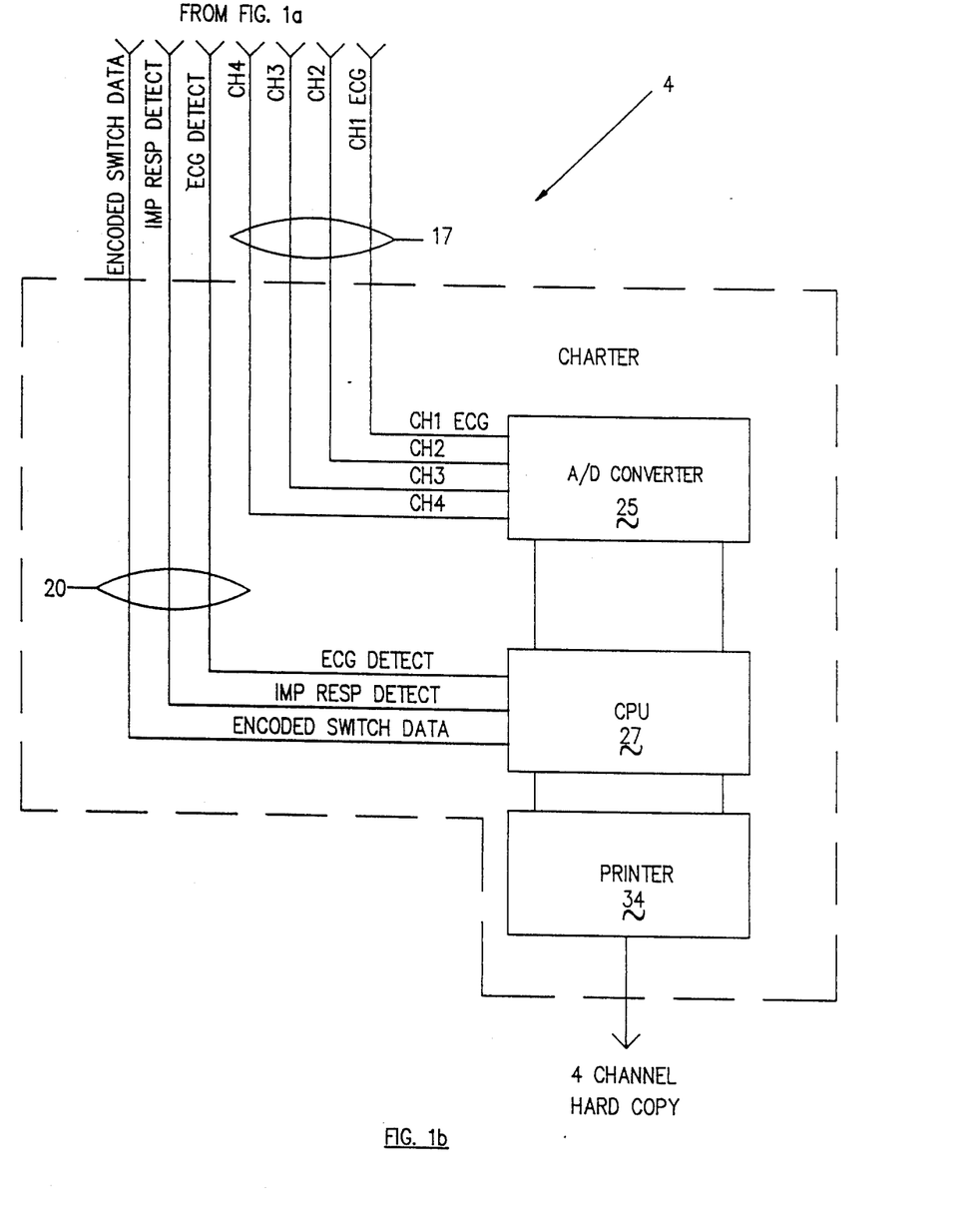
Figure 1C:
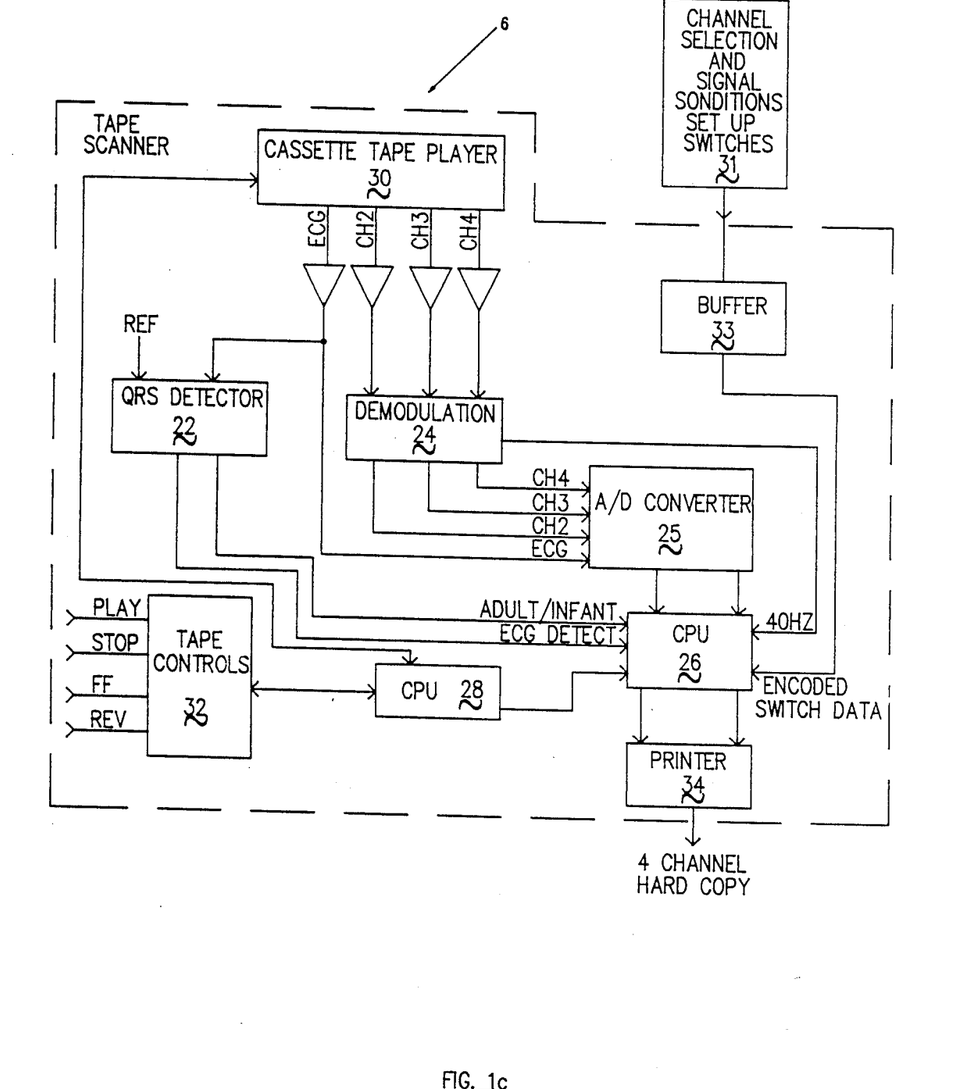

Referring to FIGS. 1a, 1b and 1c, functional block diagrams are shown of the circuitry included in the individual multi-channel recorder 2, charter 4 and tape scanner 6 devices of the present system. Each device 2, 4 and 6 is constructed as a stand-alone assembly within its own chassis. In normal use, the multi-channel recorder 2 of FIG. 1a is coupled to a plurality of sensor inputs from leads secured to the patient under study. A magnetic tape of suitable length is mounted in an associated tape drive 14 to record the collected data over the study period. Simultaneously, the charter 4 might be coupled to the tape drive inputs to chart the data directly via thermal printing onto a 4¾ inch Z-fold strip chart. Alternatively, the tape may later be replayed on the scanner 6 with the data of each channel then being charted.

Mounted on the console of the recorder 2 is a switch panel (reference channel selection/signal set up switches 31 at FIG. 1c) which provides for a plurality of selectable settings relative to the subject being monitored. That is, an infant/adult switch selects circuitry for accommodating higher ECG rates commonly associated with infants versus adults along with other signal filtering.

A calibration switch induces associated circuitry during the first six minutes of a study to produce predefined reference signals from a read only memory (ROM) which are charted on the selected charter tracks and relative to which equipment offset and gain may be ascertained and adjusted to properly print each channel's data relative to the strip chart. ECG is calibrated at 0.5mv, 120 BPM; impedance at 0.5 ohm, 30 BPM; strain gauge at 30 BPM and thermistor at 30 BPM; and O2 saturation is calibrated at 0%, 50%, 75% and 100% with calibration occurring over a three-second period at each level. Once every six minutes thereafter, the four calibration levels are rewritten. If a de-saturation event occurs (i.e. the detected level is less than 88% O2 saturation) during the time the calibration sequence is being written, the sequence is abbreviated to only 0.5 seconds per level so that a significant event is not missed.

An impedance switch permits a normal pneumogram or a low gain waveform setting. Other sensor input switches define the selection of a strain gauge or nasal thermistor, whether alarms are annunciated or not, and establish the gain level. If an oximetry sensor is used, a code may be set relative to specific manufacturer's sensor, along with whether O2 or O2 plus pulse data is monitored. Lastly, channel selector switches for tape channels 2 to 4 selectively define the various input sensors coupled thereto. Channel 1 however is always relegated to ECG data.

Once the proper switch parameters are established and the sensors are appropriately coupled to the recorder 2, the analog sensor input data is coupled by way of the channel selector and signal conditioning circuitry 12 to the appropriate data channels 1 to 4 at the tape drive 14. There the data is recorded in conventional fashion. The selector/conditioning circuitry 12 thus essentially multiplexes or couples the monitored data to a desired and calibrated channel.

Figure 2:
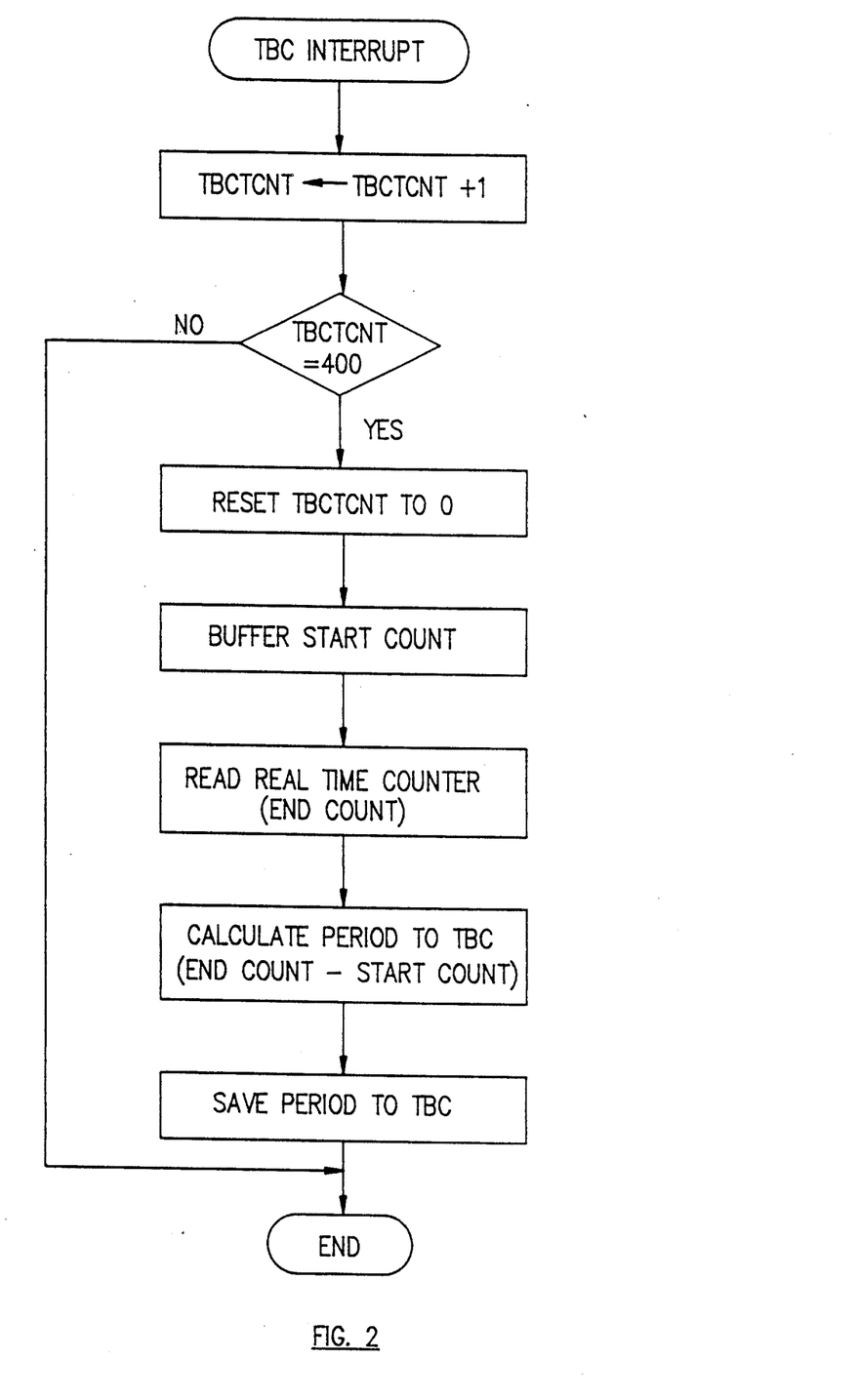
FIG. 2 shows a flow diagram of the operation of the time normalization circuitry within the recorder.

Referring also to FIG. 2 and appreciating that a variety of factors may affect data collection and replay, such as time varying tape speeds, tape stretch, etc., the recorder 2 produces a user transparent, 40Hz time base signal via a crystal oscillator 18, which normally is included with the CPU 10. By dividing down the clock output via appropriately configured counters, a periodic 25 msec time base signal is obtained which is modulated with the impedance respiration data at the selector/conditioning circuitry 12 before the modulated signal is coupled to the user defined tape channel. Because the time base signal occurs at a distinguishable frequency from the normally occurring impedance respiration signal, the time base signal does not deleteriously affect the data signal and is relatively easily demodulated by the scanner 6 during later replay In a similar fashion and appreciating that a subject's pulse rate occurs at a frequency distinguishable from the O2 saturation trend line, the O2 saturation data can be hardwire OR'ed at the selector/conditioning circuitry 12 with the pulse input waveform data and selectively displayed on a single channel, as opposed to separate channels (reference FIGS. 5d, 5e). By combining distinguishable data on single tracks, other tracks are freed up other input data, such as from a nasal/oral thermistor. Alternatively and depending upon the selected switch settings, the pulse input data may be separately displayed from the O2 saturation data (reference FIGS. 5b, 5c).

If the collected data is to be simultaneously charted, a charter 4 may also be coupled to the output bus 16 via read switch 19. Upon enabling the read switch 19 and connecting the charter 4 to a parallel coupled jack at the recorder's chasis, the data is also coupled via bus 17 to the charter's inputs. Simultaneously, the CPU 10 couples encoded switch data and detected ECG and respiration events to the charter 4 via bus 20, the reasons for which will become more apparent from the discussion of the recorder 6 of FIG. 1c.

The CPU 10 additionally monitors pulse detection signals relative to ECG detect signals to derive motion control signals which are coupled to the charter and tape. The motion control signals are particularly determined via a motion detection algorithm which equates the ECG and pulse detect signals to one another. A clinician may again selectively choose to enable this feature or not at his/her preference. A more detailed discussion follows with respect to FIG. 4.

Turning attention to FIG. 1c, a block diagram is shown of the tape scanner circuitry 6 and upon which the tapes recorded via the recorder 2 are replayed. The charter 4 of FIG. 1b includes a goodly portion of the same circuitry as in the scanner 6, except for the tape control and the circuitry in the monitor 8 and CPU 10 for demodulating the 40Hz time base signal and producing the tic marks and motion indicators. Accordingly and for convenience, the following description is only directed to the circuitry of the scanner 6 which includes the combination circuitry.

The scanner 6 particularly includes QRS detect circuitry 22 and de-modulation circuitry 24. The QRS detect circuitry 22 monitors the recorded ECG data relative to a predetermined reference threshold to produce ECG detect signals which are coupled to the scanner's CPU 26. The demodulation circuitry 24, in turn, de-modulates the impedance respiration data from the proper one of channels 2 through 4 to separate out the 40Hz time base signal, which also is coupled to the CPU 26 via the analog to digital converter 25.

Otherwise, control of tape replay is separately performed by a CPU 28 which controls the operation of the tape player 30 relative to the selected inputs at the tape controls 32. As mentioned, during scanning, a variety of selectable functions may also be enabled via the CPU 26, over and above mere tape replay, upon appropriately setting the channel and setup switches 31 provided at the scanner 6. This switch data is encoded and stored in a buffer 33.

In particular and relative to the QRS detector 22, the gain at which the detector 22 operates may be set to avoid sensing excessive false ECG signals or missing faint ECG signals, although the detector 22 is normally operated in an auto position. An infant/adult switch is provided, along with an O2 saturation scale select of either 0 to 100% or 50% to 100%. A keyboard input is also provided to permit a programmable search function relative to tape position and whereby the scanner 6 may be advanced to a desired point and time at which replay and charting may be begun. Power, tape location, search location and active channel indicators are additionally provided.

Otherwise and relative to the charting of the replayed data via printer 34, a chart/pause switch enables/disables the printing of the replayed data. The printer speed (i.e. 0.5, 1, 2, 5 and 10 mm/sec) may be selected such that the real time recorded study data may be compressed, yet still be intelligible at a resolution which displays in a meaningful fashion the recorded data. When a desired event is located, however, the chart speed may be increased to display the event in an expanded fashion (i.e. 12.5, 25 or 50 mm/sec). The normal chart speed however is 1mm/sec which equates with the scanning of a 12 hour tape in approximately 30 minutes.

Also provided are offset and gain control switches for each of the four input channels whereby the printed data may be vertically centered relative to grid tracks provided on the chart paper. FIG. 5b shows an example during a "Calibration" portion of the stored calibration signal used to set offset and gain for the pulse/oximetry channel.

In passing, it is to be noted that the printer 34 prints the four separate grid tracks which appear as a checkerboard pattern having intermediate rows and columns indicated by dotting at the same time as the data on blank chart paper at appropriate grey tones relative to the other outputs of channel data ,.and ,scale and sensor identification alpha-numerics. For drawing clarity, only a portion 13 of the grid track pattern is shown in FIG. 5b. A similar pattern otherwise normally appears with all the waveforms. A time reference indicated with short vertical has marks is also printed along the bottom chart edge, using the detected time base signal, in 10 second increments with one minute numeric notations being indicated at emboldened arrows, reference FIG. 5c. Scaling values cyclically appear in a vertical column superimposed over the data and grid tracks.

Returning attention to the CPU 26 and with additional attention to the flow diagram of FIG. 2, upon receipt of the 40Hz time base time signal from the CPU's crystal oscillator and the ECG input, the CPU 26 controls a pair of counters (not shown) to count between each input event. Each count of the time base signal counter is reflective of the period of time between each successively detected QRS complex and each of the known 40Hz time base (TBC) signal, although may be off by a clock cycle, but which at the selected clock rate is not significant. That is, the absolute value of the difference between the starting and ending counts between events for each counter are compared every 400 counts to produce an ECG beat per minute (BPM) value from the following equation 1 which reflects the ECG beat per minute (BPM) trend rate.

$$ECG_{BPM} = \frac{6 \times tbc}{t_{ECG}} \qquad \text{Eq. (1)}$$

Where $t_{ECG}$ = period of ECG interval Thus, the ECG rate in beats per minute can be simplified to a ratio of the two counts which are readily computed in the CPU 26. This data is then plotted at the thermal printer's 34 sampling rate to produce an essentially continuous trace or trend line of the heart rate.

Similarly, the analog data on each of the other channels 2 to 4 are sampled, converted to digital data and valued in magnitude relative to the operator established gain and offset and displayed on the appropriate track portions of the chart paper.

Figure 3:
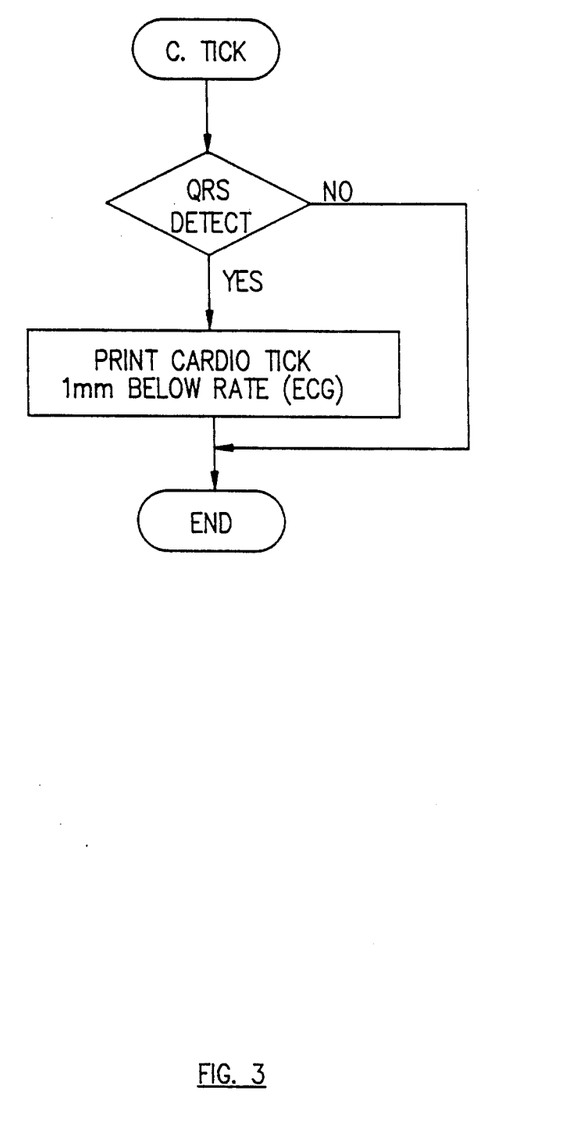
FIG. 3 shows a flow diagram of the manner in which the tape scanner and charter circuitry detect and print the hash marks corresponding to each QRS complex.

With attention next directed to FIG. 3, a flow chart is shown of the operations enabled by micro-coding stored in ROM which relative to the ECG detect signals of detector 22 and heart rate trace line, when the scanner is in a trend display mode, causes individual hash or "tic" marks to be printed on the trace line which are indicative of each detected QRS complex. That is, with the selection of a trend mode of scanner 6 operation, the CPU 26 monitors each ECG detect signal relative to a predetermined threshold magnitude and causes the printer 34 to print a 1mm vertical hash line below the then current computed rate value. Instead therefore of a continuous line, a series of hash marks are produced on the line which may be manually counted for any selected time period and extrapolated onto other data tracks to confirm the displayed rate.

Figure 5A:
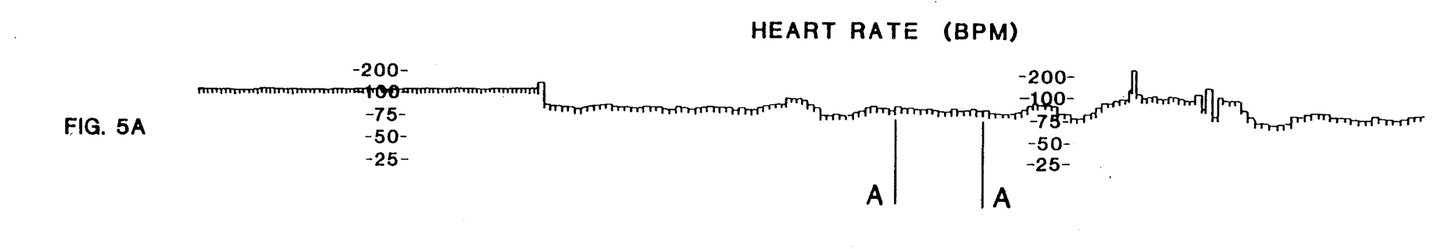
FIGS. 5a to 5d show diagramatic waveforms of charted cardiac and respiratory activity.
Figure 5B:
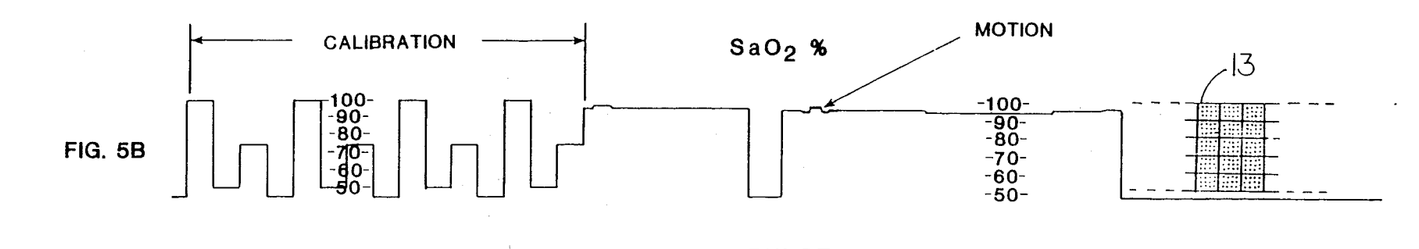
Figure 5C:
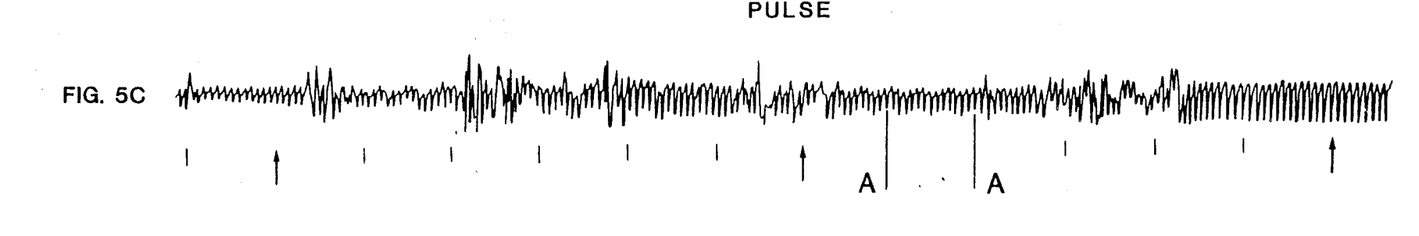
Figure 5D:
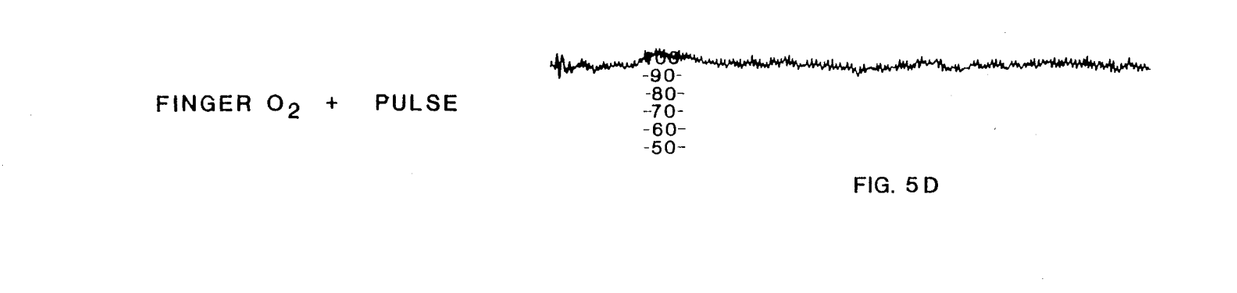

For example, the diagnostician by counting the tic marks and pulse events for a particular study between the A—A extrapolation points of the ECG, pulse and/or finger O2+pulse waveforms of FIGS. 5a and 5c can compare the pulse and ECG data to confirm,..correspondence or not. In passing, it is to be appreciated the waveforms of FIGS. 5a–5d are not from the same study and are shown only as representative indicators of the point being made.

Figure 6A:
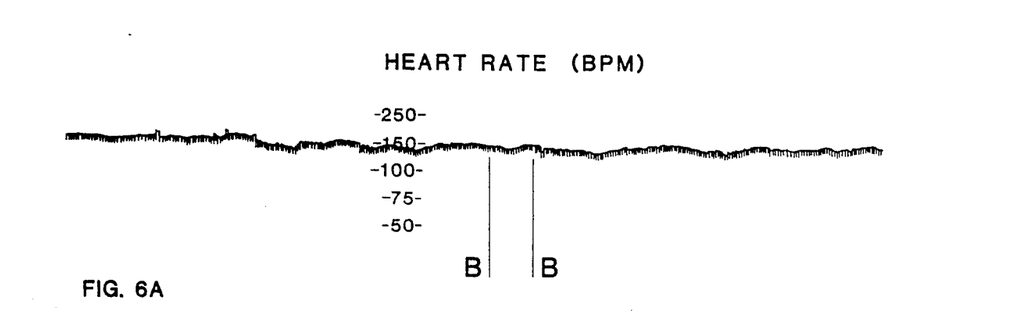
FIGS. 6a and 6b a cardiac artifact on the impedance channel.
Figure 6B:
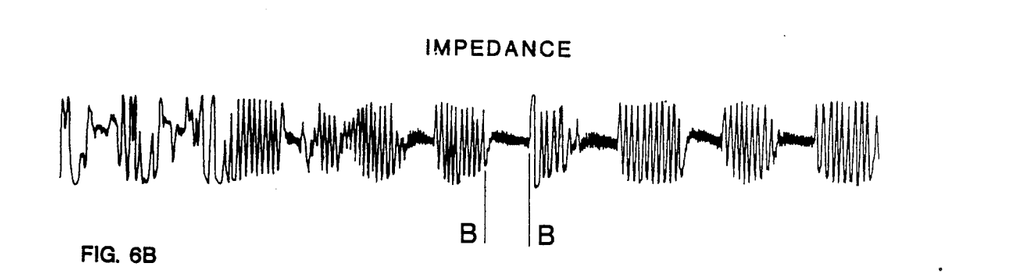

Another extrapolation of the ECG date and CARDIO TICKS onto the impedance respiration waveform from the same study and as shown in FIGS. 6a and 6b between extrapolation points B—B confirms the presence of a cardiac artifact. That is, the chest wall movement which occurs from breathing as in FIG. 6b may include movement or noise coincident with the beating of the heart which improperly appears as respiration.

Figure 7A:
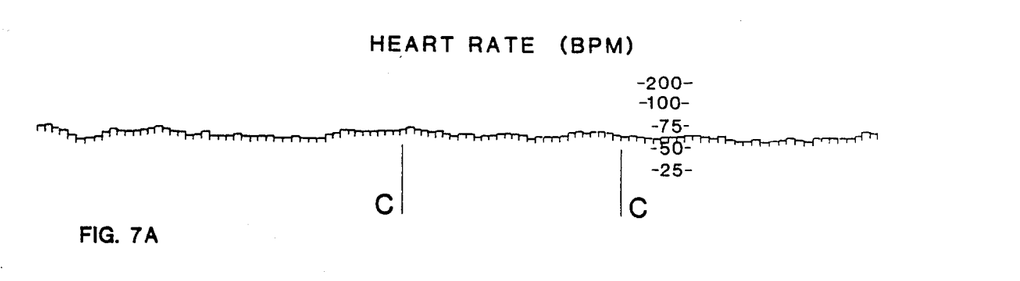
FIGS. 7a and 7b demonstrate the extrapolation of a motion artifact on the O2 channel.
Figure 7B:
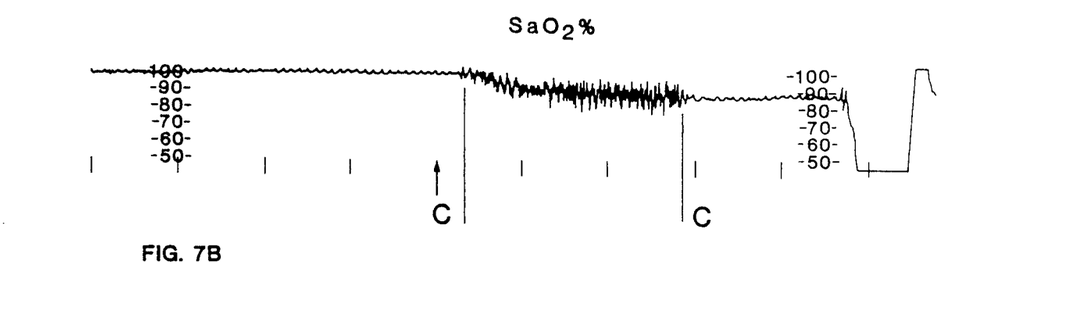

Still another extrapolation of the hash marks or CARDIO TICKS from another study onto related SaO2 data, as shown in of FIGS. 7a and 7b between extrapolation marks C—C, confirms a motion artifact or not relative to the displayed O2 saturation data.

Figure 4:
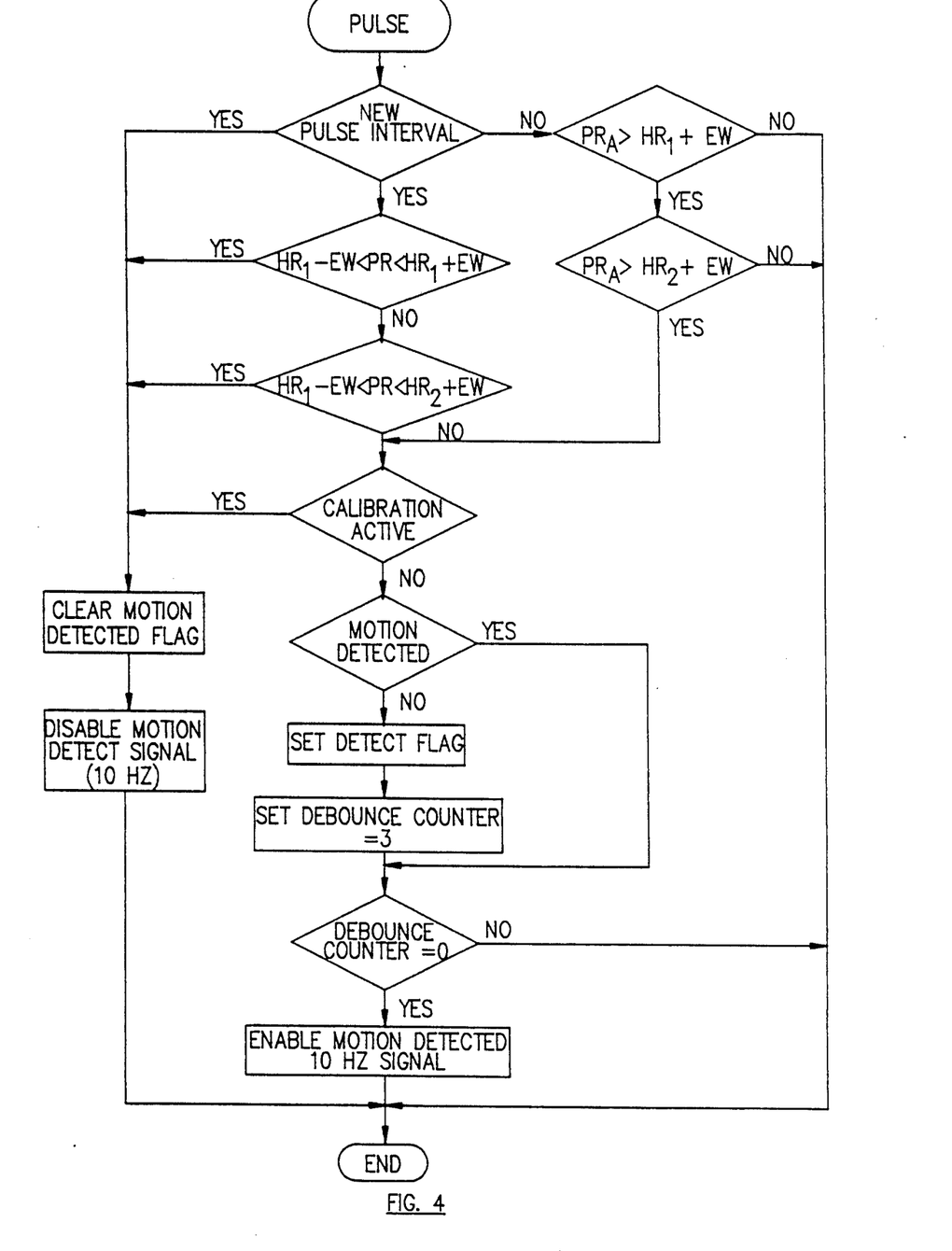
FIG. 4 shows a flow diagram of the manner in which the micro-processor multiplexes the pulse and oximetry data.

Appreciating that the clinician may select the automatic motion detection feature of the invention, attention is directed to FIG. 4 which shows a flow diagram of the manner in which motion is displayed on the O2 saturation data. A motion artifact is particularly displayed as a 10 Hz signal which is superposed over the O2 data by the CPU 26, upon comparing the ECG detect and pulse detect signals for equivalence (reference FIG. 5b). The pulse detect signals may either be separated out of the pulse oximetry data, or may be independently monitored. If a determined count value between detected ECG events and pulse detect events are not determined to be equivalent, CPU 26 calls a sub-routine which sums a 10Hz motion artifact on the pulse oximetry data. Otherwise, if near equivalence is found, no motion artifact is added.

From FIG. 4 and the following definitions,
$PR_A$: active pulse average $(PR_1 + PR_{IT})$
$PR$: $PR_1 + PR_2$
$HR_1$: $HRI_1 + HRI_2$
$HR_2$: $HRI_2 + HRI_3$
the CPU 26 essentially performs a number of comparisons of the periods between pairs of successive pulse detects $(PR_N)$ relative to successive pairs of ECG $(HRI_N)$ detects and relative to pre-defined tolerances established for various ECG rate ranges. If the average pulse rate falls within the established equivalence window for at least one of two comparisons performed over three events, no motion is shown. In the alternative, if a pulse is not detected but the ECG rate falls within the equivalence window of the prior average pulse rate, then again no motion is shown.

If motion is detected and before indicating the motion, CPU 26 also confirms that the motion has existed for at least a predetermined number of cycles. It does this by setting a counter to the predetermined number of cycles for which the motion must exist. As each subsequent motion event is confirmed, the counter is appropriately decremented or incremented. With the last confirmation of a motion detect, the motion artifact printing subroutine is initiated.

In passing and for the presently preferred embodiment, if motion is not indicated for at least three successive cycles, the motion detect flag is cleared. If too the scanner is still within its six minute calibration cycle, the CPU 26 disables the motion detect feature.

Otherwise, in a manual circumstance and with reference to FIGS. 5a and 5e, the clinician may extrapolate between the Cardio Ticks on the heart rate data track and the pulse data on a degrading O2 saturation data track to confirm correspondence directly on the chart. If correspondence between each tick mark and each pulse mark is not found, the O2 data is suspect and can be interpreted as subject motion, in contrast to a change in O2 saturation. Calibration drift in the oximetry equipment may be similarly detected and which condition is not otherwise readily detectable.

While the present invention has been described with respect to its presently preferred embodiment, it is to be appreciated still other modifications may be made thereto without departing from the spirit and scope of the following claims. It is accordingly contemplated that the following claims should be interpreted to include all those equivalent embodiments within the spirit and scope thereof.

What is claimed is:

1. Cardio respiratory monitoring apparatus comprising:
   (a) means for receiving n physiologic input signals from a plurality of transducers coupled to a study subject including at least an electrocardiographic (ECG) signal, a pulse signal, a plethysomographic signal, and an oximetry signal and an impedance respiration signal;
   (b) a clock source;
   (c) means coupled to said clock source for producing a periodic time base signal in the range of 20 to 40Hz;
   (d) means for modulating said impedance respiration signal with said time base signal;
   (e) means for selectively modulating said pulse signal with said oximetry signal; and
   (f) means for recording each of said physiologic input signals and said modulated time base signal on $n-1$ data tracks.

2. Apparatus as set forth in claim 1 including:
   (a) means for reading said recording;
   (b) means for demodulating said time base signal from said respiration signal;
   (c) means for detecting each of a plurality of cardiac complexes of the ECG signal;
   (d) means for detecting each of a plurality of pulse events of the pulse signal;
   (e) means for counting the cycles of said time base signal between each successively detected cardiac complex and pulse event; and
   (f) means for processing the count data to determine a heart rate.

3. Apparatus as set forth in claim 2 including:
   (a) means for averaging the count data between a plurality of cardiac complexes;
   (b) means for periodically comparing the averaged cardiac data relative to a predetermined range of permissible ECG activity;
   (c) means for displaying said oximetry signal; and
   (d) means for overlaying a predetermined artifact signal on said respiration signal, if said comparator means does not detect equivalence.

4. Apparatus as set forth in claim 1 wherein said motion signal comprises a 10Hz signal.

5. Apparatus as set forth in claim 2 including:
   (a) means for displaying the heart rate as a continuous cardiac trace line; and
   (b) means responsive to the detection of each cardiac complex for overlaying an identical hash mark on said cardiac trace line in correspondence with each cardiac complex.

6. Apparatus as set forth in claim 5 wherein said hash mark is orthogonal to said cardiac trace line.

7. Cardiac respiratory monitoring apparatus comprising:
   (a) means for receiving n physiologic input signals from a plurality of transducers coupled to a study subject including an electrocardiographic (ECG) signal, a pulse signal, a plethysomographic signal, and an oximetry signal and an impedance respiration signal;
   (b) a clock source;
   (c) means coupled to said clock source for producing a 40Hz time base signal;
   (d) means for modulating said impedance respiration signal with said time base signal; and (e) means for recording each of said physiologic input signals and said modulated time base signal on n data tracks;

(f) means for demodulating said time base signal from said respiration signal;

(g) means for detecting each of a plurality of QRS complexes of the ECG signal;

(h) counter means for counting the cycles of said time base signal between each successively detected QRS complex and pulse event to determine a count for each ECG interval; and (i) means for periodically determining the heart rate of the study subject from a ratio of 240 divided by the determined ECG interval.

8. Cardio respiratory monitoring apparatus comprising:

(a) means for receiving n physiologic input signals from a plurality of transducers coupled to a study subject;

(b) a clock source;

(c) means coupled to said clock source for producing a periodic time base signal;

(d) means for modulating y distinguishable ones of said n physiologic input signals with others of said input signals, including said time base signal; and (e) means for recording each of said n physiologic input signals and said time base signal on n-y data tracks.

9. Apparatus as set forth in claim 8 including:

(a) means for reading said recording;

(b) means for demodulating selected ones of the modulated input signals and said time base signal; and (c) means for charting each of said modulated and demodulated data tracks relative to said time base signal.

10. Apparatus as set forth in claim 8 wherein one of the physiologic input signals is an electrocardiographic (ECG) signal containing individually detected QRS complexes and including:

(a) means responsive to the ECG signal for displaying the cardiac rate as a continuous trace line; and (b) means responsive to each QRS complex for displaying an identical hash mark on the cardiac trace line in correspondence therewith.

11. Cardio respiratory monitoring apparatus comprising:

(a) means for receiving n physiologic input signals from a plurality of transducers coupled to a study subject;

(b) a clock source;

(c) means coupled to said clock source for producing a periodic time base signal;

(d) means for modulating said time base signal with at leas tone of said n physiologic input signals; and (e) means for recording each of said physiologic input signals and said modulated time base signal on n data tracks.

12. A method in a cardio respiratory charting system for displaying a motion artifact of a study subject, comprising the steps of:

(a) monitoring an input representative of cardiac activity;

(b) monitoring an input representative of pulsed blood in the subject;

(c) continuously determining a relative indication of a period between successive cardiac events and pulse events;

(d) comparing the period of each successive cardiac and pulse event for equivalence; and (e) displaying detected periods of inequivalence as a predetermined trace signal relative to a displayed trace signal of an oximetry input signal.

13. A method in a cardiac respiratory charting system for displaying cardiac activity, comprising the steps of:

(a) monitoring an input representative of cardiac activity;

(b) monitoring a time signal recorded simultaneously with said cardiac input;

(c) determining and displaying a continuous trace indicative of the rate trend of the cardiac input;

(d) detecting each QRS complex of the cardiac activity; and (e) displaying each QRS complex as a hash mark.

* * * * *